(12) United States Patent
Sperling et al.

(10) Patent No.: US 6,979,729 B1
(45) Date of Patent: Dec. 27, 2005

(54) METAL CLUSTER CONTAINING NUCLEOTIDES AND NUCLEIC ACIDS, AND INTERMEDIATES THEREFOR

(75) Inventors: Joseph Sperling, Jerusalem (IL); Ohad Medalia, Yarkona (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 383 days.

(21) Appl. No.: 10/070,728

(22) PCT Filed: Sep. 13, 2000

(86) PCT No.: PCT/IL00/00564

§ 371 (c)(1),
(2), (4) Date: Mar. 11, 2002

(87) PCT Pub. No.: WO01/20017

PCT Pub. Date: Mar. 22, 2001

(30) Foreign Application Priority Data

Sep. 14, 1999 (IL) .............................................. 131889

(51) Int. Cl.⁷ ....................... C07H 21/00; C07H 21/02; C07H 21/04; C12Q 1/68

(52) U.S. Cl. ..................... 536/23.1; 536/24.3; 536/25.3; 536/36.6; 435/6

(58) Field of Search ....................... 435/6, 16; 536/23.1, 536/24.3, 25.3, 26.6, 25.33; 530/391.5, 391.9; 436/94; 424/1.29, 1.53

(56) References Cited

U.S. PATENT DOCUMENTS

| 6,008,334 A | * 12/1999 | Hanna ....................... 536/22.1 |
| 6,265,558 B1 | * 7/2001 | Cook et al. ................. 536/23.1 |
| 6,369,206 B1 | * 4/2002 | Leone et al. .............. 530/391.5 |

* cited by examiner

*Primary Examiner*—Jezia Riley
(74) *Attorney, Agent, or Firm*—G.E. Ehrlich (1995) Ltd.

(57) ABSTRACT

Nucleotides including a sugar moiety, a pyrimidine or purine base and a terminal thiol group at a side chain covalently linked to pyrimidine or purine base of the nucleotide, and optionally further including a metal cluster covalently linked through the terminal thiol group at said side chain to the pyrimidine or purine base of the nucleotide, and nucleic acids incorporating same.

21 Claims, 3 Drawing Sheets

(3 of 3 Drawing Sheet(s) Filed in Color)

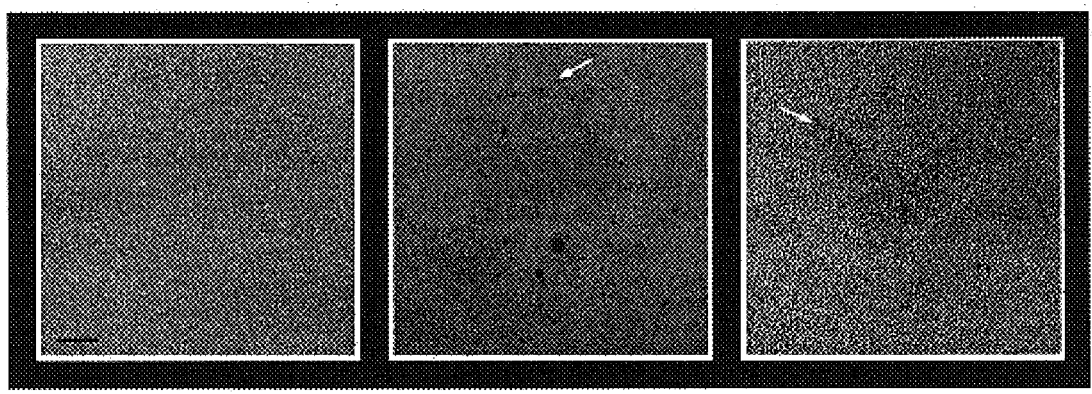
Fig. 3a   Fig. 3b   Fig. 3c
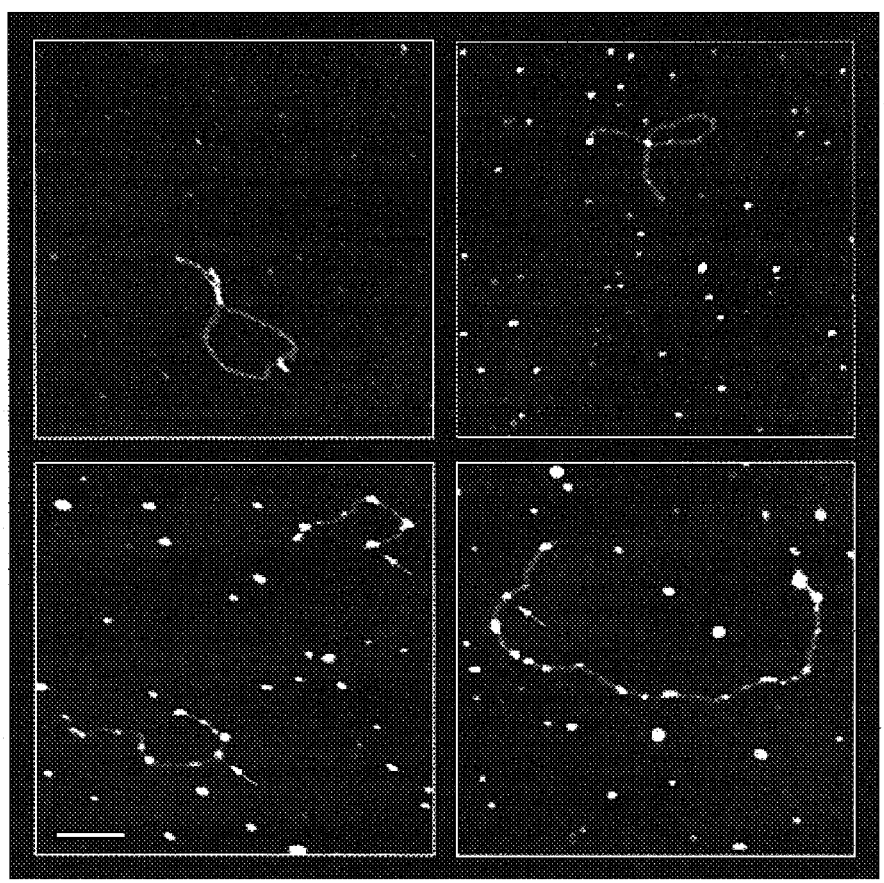
Fig. 4a
Fig. 4b

METAL CLUSTER CONTAINING NUCLEOTIDES AND NUCLEIC ACIDS, AND INTERMEDIATES THEREFOR

FIELD OF THE INVENTION

The present invention relates to nucleotides comprising a terminal thiol group, to such nucleotides further comprising a metal cluster, preferably a gold cluster, covalently attached through said terminal thiol group, and to nucleic acids comprising at least one of the described nucleotides.

BACKGROUND OF THE INVENTION

Protein-ribonucleic acid (RNA) interactions play a key role in many fundamental life processes In living organisms, these polymers are often found complexed together in extremely large assemblies whose molecular mass may reach several millions of daltons. In the pathway of gene expression one finds transcribing complexes, containing RNA polymerase in action on a DNA template, with associated nascent RNA. Concurrently, the resulting precursor messenger RNA (pre-mRNA) becomes associated with a multitude of proteins and additional small RNA molecules into a large ribonucleoprotein (RNP) complex, the spliceosome, where it is processed to mature mRNA. Protein synthesis then takes place in the cytoplasm on a third class of particles—the ribosomes. In addition, a number of large protein complexes require mononucleotides (e.g., ATP, GTP) for their assembly and/or catalytic activity.

For such inherently polymorphic assemblies, visualization by transmission electron microscopy (TEM) provides structural information at a resolution that is difficult to obtain in any other way (Chiu and Schmid, 1997; Griffith et al., 1997). Yet, localization and tracing by electron microscopy of RNA or ribonucleotides within such large biological assemblies, are not yet a straightforward undertaking. Even when crystals amenable to X-ray crystallography analysis can be obtained, as is the case for ribosomes, there is still a demand for heavy atom derivatives to phase the diffraction data (Weinstein et al, 1992). Covalent derivatization of RNA with heavy atoms should enable visualization of RNA within RNP complexes by EM and ensure the introduction of electron-dense centers at distinct locations within crystallized RNA molecules and RNP complexes.

Visualization of nucleic acid molecules by TEM cannot be directly achieved because of the low-density weakly scattering atoms they contain. Nevertheless, methods such as electron spectroscopic imaging (e.g., Bazett-Jones, 1992), tungsten shadow casting (e.g., Wang et al., 1994), atomic force microscopy (AFM; e.g. Hansma et al., 1996; Smith et al., 1997), and scanning tunneling microscopy (e.g., Guckenberger et al., 1994) have been used to visualize naked RNA and DNA molecules. More recently, a positive staining protocol that allows visualization of nucleic acids (Dubochet et al., 1971) was used to visualize RNA strands emanating from supraspliceosome particles (Muller et al., 1998), yet RNA located within the particles was not visible. Tagging such macromolecules with clusters of heavy atoms should facilitate their visualization by conventional TEM. The present most popular method employs colloidal gold non-covalently attached to specific antibodies, protein A or other macromolecular probes. For example, attempts were made to visualize spliceosomes by dark-field scanning transmission electron microscopy (STEM) after tagging with biotinylated oligonucleotides complementary to the pre-mRNA that had been conjugated to a streptavidin-colloidal gold complex (Sibbald et al., 1993).

The use of probes with covalently conjugated gold compounds provides a number of advantages over colloidal gold. These include better stability, size uniformity, and complete absence of aggregation, all of which result in better sensitivity and resolution. A number of gold clusters containing a core of 11 gold atoms surrounded by a hydrophilic organic shell of aryl-phosphines have been described (Safer et al., 1986). These undecagold compounds have the general formula $Au_{11}L_6L'X_3$, where L is tris(4N-methylcarboxamidophenyl)phosphine, and L' is a similar ligand in which the methylcarboxamido group on one of the benzene rings is replaced by an activatable side chain such as an ω-amino alkyl group. Activation of this compound with a maleimido group yields a gold cluster that can be conveniently coupled to free thiol groups of proteins (Safer et al., 1986; Wenzel and Baumeister, 1995). An interesting example is the specific labeling with undecagold of the ribosomal protein BL11 within the 50S ribosomal subunit of *Bacillus stearothermophilus* for its subsequent use as a heavy atom derivative for crystallographic studies (Weinstein et al., 1989, 1992). The same authors also labeled $tRNA^{phe}$ of the same organism by taking advantage of the modified nucleoside 3-(3-amino-3-carboxypropyl) uridine at position 47. The exposed primary amine of this base was reacted with 2-iminothiolane to extend the aliphatic chain and introduce a primary thiol group, which was then coupled to maleimido undecagold (Weinstein et al., 1992).

The diameter of the undecagold cluster is 0.82 nm. It can thus be visualized by high-resolution STEM, but not readily by conventional TEM unless the signal is enhanced by silver enhancement (Burry et al., 1992). Visualization by conventional TEM can be improved by using a larger, 1.4 run. gold cluster (Hainfeld and Furuya, 1992). The structure of this reagent, now commercially available from Nanoprobes (Stony Brook, N.Y.) under the trademark "NANOGOLD". has not yet been reported. It has nevertheless been used successfully to label proteins (Boisset et al., 1992; Hainfeld and Furuya, 1992) as well as the 5' or 3' ends of DNA oligonucleotides (Alivisatos et al., 1996).

The present invention teaches a general systematic strategy for incorporating gold clusters into nucleotides and nucleic acid molecules.

SUMMARY OF THE INVENTION

The present invention provides, in one aspect, a nucleotide comprising a terminal thiol group at a side chain covalently linked to the pyrimidine or purine base of the nucleotide.

In one embodiment, the sugar moiety of the nucleotide of the invention is ribose; in another embodiment, the sugar moiety is deoxyribose, dideoxyribose or any other ribose analog. The nucleotide of the invention may be a monophosphate, a diphosphate, a 3',5'-bisphosphate or a 5'-triphosphate.

The side chain of the nucleotide of the invention carrying the terminal thiol group may be saturated or unsaturated and has 2–20, preferably 2–15, most preferably 2–10, carbon atoms, optionally interrupted by heteroatoms selected from O, S or N and/or substituted by groups such as =O, =NH and/or 1–3 alkyl groups.

In another aspect, the invention relates to a nucleotide having a metal cluster covalently linked through a terminal thiol group of a side chain covalently linked to the pyrimidine or purine base of the nucleotide The metal may be Ag, Au, Hg, Pt, Mo or W, but is preferably a gold cluster such as colloidal gold.

In a further aspect, the invention relates to a nucleic acid comprising at least one nucleotide of the invention comprising a free terminal thiol group or a metal cluster covalently linked through a terminal thiol group. The nucleic acid may be a RNA or a DNA molecule.

In one embodiment, the nucleic acid molecule is covalently tagged with a metal cluster. The metal may be Ag, Au, Hg, Pt, Mo or W, but is preferably a gold cluster such as colloidal gold.

The metal-tagged nucleic acids of the invention are useful as probes for macromolecular assemblies such as protein-RNA complexes.

The invention provides general methodologies for the covalent attachment of gold-clusters to DNA and RNA (nucleic acids) at random locations as well as at specific locations.

The general strategy for the attachment of gold-clusters at random locations in the nucleic acid molecule is depicted in Scheme I and involves the following steps:

(i) preparation of precursor deoxyribonucleoside triphosphates (NTPs) and ribonucleoside triphosphates (rNTPs) whose heterocyclic ring contains substituents with a terminal thiol group (NTP-SH and rNTP-SH. respectively);

(ii) incorporation of these precursor molecules in DNA or RNA in reactions catalyzed by DNA polymerase or RNA polymerase, respectively; and (iii) attachment of gold-clusters to the free thiol groups, either by reacting with a commercially available maleimido derivative of the cluster, or by reacting with colloidal gold of pre-determined size.

The strategy for the attachment of a gold cluster to a specific location in the nucleic acid molecule is depicted in Scheme 2 and involves the following steps:

(i) preparation of 3',5' deoxyribonucleoside diphosphates (p[dN]p) and 3', 5' ribonucleoside diphosphates (pNp) whose heterocyclic ring contains substituents with a terminal thiol group (p[dN]p-SH and pNp-SH, respectively);

(ii) synthesis of the 5' half of the nucleic acid whose 3' end nucleotide is the one that precedes the nucleotide to which a gold cluster should be attached;

(iii) addition of p[dN]p-SH or pNp-SH to the nucleic acid made in (ii) by using the DNA ligase or RNA ligase, respectively; and (iv) dephosphorylation of the 3' end of the nucleic acid made in (iii), and ligating it to the 3' half of the nucleic acid.

Ribonucleic acids (RNAs) play a key role in many fundamental life processes. These polymers are often found complexed with proteins in extremely large particles whose molecular mass may reach several millions of daltons (e.g., ribosomes, spliceosomes, and viruses). Structural studies of such RNA-protein complexes should help elucidate their mode of action. For the structural analyses of many macromolecular assemblies, electron microscopy (EM) has served an instrumental role. However, localization by EM of RNA within biological complexes is not yet a straightforward undertaking. Here we describe a methodology for the covalent tagging of RNA molecules with gold clusters, thereby enabling their direct visualization by microscopical methods. The strategy involves transcription in vitro of RNAs that carry free thiol groups, using ribonucleoside triphosphate analogs containing a substituent with a terminal thiol group on their heterocyclic ring. This synthesis is followed by coupling of gold clusters to the thiolated transcript through a maleimido group. Visualization of such gold-tagged RNAs by transmission electron microscopy showed spots of gold clusters, with a diameter of 1–2 nm, arranged at nearly regular distances on an imaginary curve that corresponds to the RNA chain. This assignment was corroborated by atomic force microscopy that exhibited images of RNA chains in which knob-like structures, whose height corresponds to the diameter of the gold clusters, were clearly seen. This invention demonstrates the potential use of nucleic acids that are covalently labeled with gold clusters for the structural characterization of protein-RNA complexes and in microelectronic devices.

BRIEF DESCRIPTION OF THE DRAWINGS

The file of this patent contains at least one drawings executed in color photograph. Copies of this patent with color photograph(s) will be provided by the Patent and Trademark Office upon request and payment of necessary fee.

FIG. 3 Transmission electron microscopy (TEM) images of unstained β-globin pre-mRNA transcripts. RNA was transcribed in vitro, treated with monomaleimido NANOGOLD, and visualized by bright-field TEM. (a) Unmodified RNA; (b) RNA transcribed in the presence of ATP-SH (10% of total input ATP); (c) RNA transcribed in the presence of UTP-SH (50% of total input UTP). Arrows indicate the RNA termini. Scale bar, 15 nm.

FIG. 4 Atomic force microscopy (AFM) images of β-globin pre-mRNA. (a) Unmodified single-stranded RNA; (b) Gold-labeled single-stranded RNA. Black to white spans 6 nm. Scale bar, 100 nm.

DESCRIPTION OF THE PREFERRED EMBODIMENTS

Figure 1:
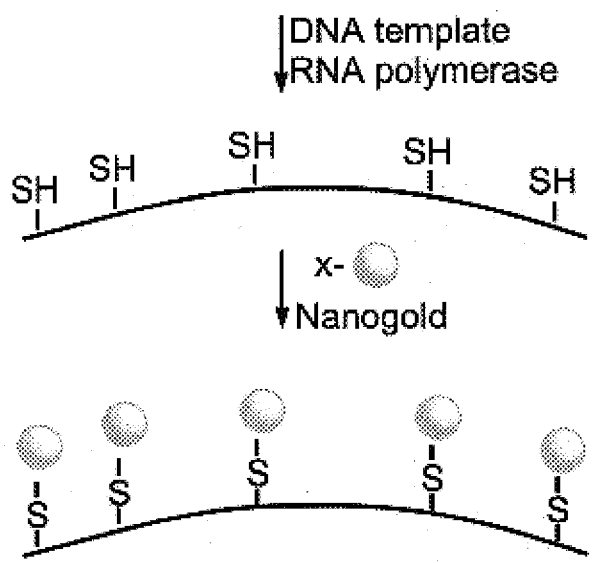
FIG. 1 A synthetic route for the preparation of gold-tagged RNAs. A nucleoside triphosphate (NTP) analog containing a substituent with a terminal thiol group on its heterocyclic ring (NTP-SH) is incorporated into RNA in a standard run-off transcription reaction, driven by RNA polymerase and using an appropriately cut plasmid as a template for transcription. The thiolated RNA molecules thus obtained are subsequently coupled through their thiol groups to a gold cluster containing a maleimido functional group to yield the gold-tagged RNA.

The present invention is of nucleotides comprising a terminal thiol group and of nucleotides further comprising a metal cluster, preferably a gold cluster, covalently attached through the terminal thiol group and of nucleic acids comprising at least one, preferably a plurality of the described nucleotides. The present invention can be used in applications in which a metal atom is more readily detectable. such as TEM and X-ray crystalography, so as to allow for improved structural analysis of nucleic acids when complexed with other macromolecules such as proteins.

Methods of labeling oligonucleotides or tRNA with metal atoms are known in the art, yet these methods are limited to either introduction of such atoms onto an existing nucleic acid molecule or introduction of such atoms to a terminal end of an existing nucleic acid molecule.

While conceiving the present invention, it was realized that if nucleotides to which a metal cluster is covalently linked were available, one could, using conventional template dependent (e.g., DNA and RNA polymerases, reverse transcriptase, etc.) or independent polymerase (e.g., terminal transferase) based techniques and/or synthetic solid phase based techniques, to synthesize nucleic acids in which the positions of the metal clusters are selected either at random, specific to certain preselected purine or pyrimidine nucleotides, or at known positions along a nucleic acid molecule.

While reducing the present invention to practice, a model approach of ribonucleotides and RNA labeled with gold clusters was chosen, yet, as will be appreciated by one of ordinary skills in the art, deoxynucleotides, as well as nucleotide analogs, such as, but not limited to, dideoxy nucleotides and nucleic acid polymers containing same can also be prepared and employed as described herein.

As used herein in the specification and in the claims section that follows, the terms "nucleotide" or in plural "nucleotides" include native (naturally occurring) nucleotides, which include a nitrogenous base selected from the group consisting of adenine, thymidine, cytosine, guanine and uracil, a sugar selected from the group of ribose and deoxyribose (the combination of the base and the sugar is known as nucleoside), and one to three phosphate groups, and which can form phosphodiester internucleosidyl linkages. However, these terms, as used herein, further include nucleotide analogs. Such analogs can have a sugar analog, a base analog and/or an internucleosidyl linkage analog. In addition, analogs exhibiting non-standard base pairing, such as described in, for example, U.S. Pat. No. 5,432,272, which is incorporated herein by reference, are also included under these terms. Thus, as used herein these terms read on molecules capable of, while incorporated in a polymer, conventional or unconventional pairing via hydrogen bonding with naturally occurring nucleotides or with nucleotide analogs exhibiting non standard base pairing and which are present in a complementary polymer.

As used herein, the term "nucleotide analog" includes nucleotides that are chemically modified in the natural base (hereinafter "base analogs"), in the natural sugar (hereinafter "sugar analogs"), and/or in the natural phosphodiester or any other internucleosidyl linkage (hereinafter "internucleosidyl linkage analogs").

Examples of base analogs that can be used according to the invention include, but are not limited to, modified purine and pyrimidine bases such as, for example, O-methyl, C-methyl, N-methyl, deaza, aza, halo. (F, Br, I), thio, oxo, aminopropenyl, amino, acyl, propynyl, pentynyl, and etheno base derivatives, as well as more drastic modifications such as replacement of the base by phenyl, and additional analogs as described in Eaton, (1997); Benner et al, (1998); Earnshaw & Gait, (1998) and Sakthivel & Barbas (1998).

Examples of sugar analogs that can be used according to the invention include, but are not limited to, modifications of the β-ribofuranosyl and β-2'-deoxyribofuranosyl sugar residues such as, for example, 2'-O-methyl, 2'-O-allyl, 2'-O-amino, 2'-deoxy-2'-halo (F, Cl, Br, I), 2'-deoxy-2'-thio, 2'-deoxy-2'-amino and dideoxy derivatives, as well as corresponding α-anomers and hexose analogs, and additional analogs as described in Eaton, (1997); Benner et al., (1998); Earnshaw & Gait, (1998); Groebke et al., (19) and Sakthivel & Barbas (1998).

Examples of internucleosidyl analogs that can be used according to the invention include, but are not limited to, those in which the natural phosphodiester linkage is replaced by a linkage such as phosphorothioate, phosphorodithioate, phosphoroamidate, methylphosphonate, and additional analogs as described in Eaton, (1997); Benner et al., (1998); Earnshaw & Gait, (1998) and Sakthivel & Barbas (1998).

Also can be used peptide nucleic acids (PNA), in which the entire phosphate-sugar backbone is replaced with a backbone consisting of (2-aminoethyl) glycine units to which bases are attached through methylenecarbonyl bridges and nucleotide analogs which are designed for solid phase synthesis of oligonucleotides, including oligodeoxynucleotides and oligodeoxyribonucleotides.

Thus, according to one aspect of the present invention there is provided a nucleotide, as this term is defined above, comprising a terminal thiol group at a side chain, which side chain is covalently linked to the pyrimidine or purine base (including analog) of the nucleotide. According to a preferred embodiment of the present invention, the sugar moiety of the nucleotide is ribose, deoxyribose, dideoxyribose or any other ribose analog. The nucleotide of the invention may be a monophosphate, a diphosphate, a 3', 5'-bisphosphate, or a 5'-triphosphate. Analogs, as is further detailed above may also be used.

The side chain of the nucleotide of the invention carrying the terminal thiol group may be saturated or unsaturated and has 2–20, preferably 2–15, most preferably 2–10, carbon atoms, optionally interrupted by heteroatoms such as O, S or N and/or substituted by groups such as $=O$, $=NH$ and/or 1–3 alkyl groups. Examples of the nucleotides of the invention are shown in Schemes 3–5 hereinbelow.

In another aspect, the invention relates to a nucleotide having a metal cluster covalently linked through a terminal thiol group of a side chain covalently linked to the pyrimidine or purine base of the nucleotide. The metal may be Ag, Au, Hg, Pt, Mo or W, but is preferably a gold cluster such as colloidal gold.

In a further aspect, the invention relates to a nucleic acid comprising at least one nucleotide of the invention comprising a free terminal thiol group or a metal cluster covalently linked through a terminal thiol group. The nucleic acid may be a RNA or a DNA molecule.

In one embodiment, the nucleic acid molecule is covalently tagged with a metal cluster. The metal may be Ag, Au, Hg, Pt, Mo or W, but is preferably a gold cluster such as colloidal gold.

The metal-tagged nucleic acids of the invention are useful as probes for macromolecular assemblies such as protein-RNA complexes.

The invention provides general methodologies for the covalent attachment of gold-clusters to DNA and RNA (nucleic acids) at random locations as well as at specific locations.

The general strategy for the attachment of gold-clusters at random locations in the nucleic acid molecule is depicted in Scheme 1 and involves the following steps:

(i) preparation of precursor deoxyribonucleoside triphosphates (NTPs) and ribonucleoside triphosphates (rNTPs) whose heterocyclic ring contains substituents with a terminal thiol group (NTP-SH and rNTP-SH, respectively);

(ii) incorporation of these precursor molecules into DNA or RNA in reactions catalyzed by DNA polymerase or RNA polymerase, respectively; and (iii) attachment of gold-clusters to the free thiol groups, either by reacting with a commercially available maleimido derivative of the cluster, or by reacting with colloidal gold of pre-determined size.

The strategy for the attachment of a gold cluster to a specific location in the nucleic acid molecule is depicted in Scheme 2 and involves the following steps:

(I) preparation of 3', 5' deoxyribonucleoside diphosphates (p[dN]p) and 3', 5' ribonucleoside diphosphates (pNp) whose heterocyclic ring contains substituents with a terminal thiol group (p[dN]p-SH and pNp-SH, respectively);

(ii) synthesis of the 5' half of the nucleic acid whose 3' end nucleotide is the one that precedes the nucleotide to which a gold cluster should be attached;

(iii) addition of p[dN]p-SH or pNp-SH to the nucleic acid made in (ii) by using the DNA ligase or RNA ligase, respectively; and (iv) dephosphorylation of the 3' end of the nucleic acid made in (iii), and ligating it to the 3' half of the nucleic acid.

The present invention provides the first description of a general methodology to covalently label synthetic nucleic acids with metal clusters. The invention is exemplified with respect to RNA labeled with gold clusters. However, in an analogous manner, it may be employed to label DNA molecules; namely, by using thiolated dNTP precursors in DNA polymerase driven reactions. The generality of the method is also manifested by the possibility it offers to label nucleic acids with clusters of heavy atoms others than gold.

Though colloidal gold was previously used to noncovalently label RNA and protein RNA complexes, it seems likely that the covalent binding of gold or other heavy metal clusters to biological assemblies of nucleic acids and proteins is advantageous. First, the binding is stable and direct in the sense that it does. not require secondary molecules such as antibodies or biotin-avidin complexes. Second, the metal clusters are relatively small and uniform in size and do not tend to aggregate. These features should provide better sensitivity and resolution to the method. Further, the methodology enables the labeling of specific residues along the nucleic acid chain (e.g., uridines or adenosines) and also to vary the density of the label by varying the concentration of the thiolated nucleotide during the enzymatically driven polymerization.

The number of studies of biologically important protein-RNA complexes is increasing rapidly. The extremely large size of many of these complexes makes the use of microscopic methods essential. The precise location and defined size of the gold label make this modification suitable for following the RNA path not only within naked RNA, as demonstrated here, but should also allow microscopic visualization of RNA within protein RNA complexes. For example, visualization of gold-tagged RNA within unstained frozen hydrated RNP complexes. This methodology is also applicable to help with phase determination in crystals of RNA-protein complexes and also in crystals of RNA molecules such as ribozymes.

The general methodology described here is designed to prepare gold-tagged RNAs in which gold clusters are randomly distributed along the RNA chain. Further developments include the preparation of RNA or DNA molecules tagged with gold clusters at specific locations. This allows the localization of specific nucleotides, or sequences of physiological importance, within a large variety of protnucleic acid complexes, which is a key step toward understanding the mechanism of action of such macromolecular assemblies.

The methodology of the present invention enables visualization of nucleic acids complexed with proteins by electron microscopy as well as use in microelectronic devices.

Progress in silicon-based microelectronics has led to the shrinkage of the characteristic size of a transistor to 0.25 microns in present days technology. It is projected that in the course of the next decade this size will be reduced to ~0.1 microns. However, major fundamental physical considerations make further size reduction very unlikely. It is therefore anticipated that a new and different technology will be needed to reduce the transistor size beyond the 0.1 microns limit. Biological-molecules based technology is a promising candidate for this length scale.

A possible approach to realize a sub-0.1 microns transistor is the single electron transistor (SET). This transistor consists of a conducting small island weakly coupled (by tunneling) to two metal contacts. The current through the island is of single electrons, which tunnel in and out of the island. This current is controlled by a metal gate, which can switch in on or off. The required size of the island for a room temperature operation of the SET is ~10 nm.

The present invention enables forming a structure of a gold cluster at a chosen location on a nucleic acid molecule (DNA or RNA). This can be the critical building block for a SET, with the cluster being the metallic island. To realize the transistor one has lo construct a structure of two contacts with a very small spacing between them, of the order of ~10 nm, and bind the two ends of the nucleic acid molecule to these contacts. The length of the molecule (and correspondingly the distance between the contacts) defines the tunneling of electrons from the gold cluster to the nearby contacts.

The important properties of the present invention for realizing such a device are the ability to determine the island size in the run range, the ability to fix its location on the molecule with a very high accuracy, the ability to determine the molecule length, and the ability to control the specific location on the molecule, which will bind to the metallic contacts.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Synthesis of thiolated UTP (Scheme 3)

1a. Synthesis of 5-Aminoallyl-UTP

5-Aminoallyl-UTP was synthesized as described by Langer et al. (Langer et al., 1981). In brief, a mixture of 275 mg of UTP (0.5 mmole, Sigma) and 0.8 gr of mercuric acetate in 50 ml of 0.1 M sodium acetate, pH 6, was stirred at 50° C. for 4 h and cooled on ice. Quantitative formation of the 5-mercurated UTP intermediate was confirmed by TLC analysis on a PEI cellulose plate in 0.75 M $KH_2PO_4$, pH 3.4 ($R_f$ 0.1) where UTP migrates with an $R_f$ value of 0.72. Lithium chloride (196 mg) was added to the chilled reaction mixture followed by 6 extractions with 50 ml ethyl acetate. The aqueous layer was added to 150 ml of ice cold ethanol, the precipitate was collected, washed with ether and dried under vacuum. The product was resuspended in 25 ml of 0.1 M sodium acetate, pH 5, and nine-fold molar excess of allyl amine (Merck, neutralized with acetic acid) was added followed by one equivalent of $K_2PdCl_4$ (163 mg, Aldrich). The reaction mixture was stirred for 24 h at room temperature and was then loaded on a column (50 ml bed volume) of Sephadex A-25 equilibrated with 20 mM triethylamoniumbicarbonate, pH 7.8 (TEAB). The column was washed with the same buffer and then developed with a gradient of 0.15–0.8 M TAB. 5-Aminoallyl UTP was eluted at 0.3–0.37 M salt. The peak fractions were combined and lyophilized, and the resulting powder was resuspended in water and re-lyophilized. This procedure was repeated 4–5 times until most of the salt evaporated. The structure of the product was confirmed by UV and 2D PMR spectroscopy.

In a similar way, other compounds carrying a radical $CH_2=CH-(CH_2)_n-NH_2$, wherein n>1, can replace allylamine (n=1).

1b. Synthesis of 5-Thiol-UTP

5-Aminoallyl UTP (0.1 mmole) was dissolved in 8 m$H_2O$ and transferred into a glass tube containing 2 ml of 1 M triethanol amine, pH 8.4, 0.25 M KCl and 25 mM Mg(OAc)$_2$. A solution of 2-iminothiolane-HCl (274 mg, Sigma) in 0.5 ml of the same buffer was added, the reaction mixture was left at 0° C. for 5–15 h and was then loaded on a column (50 ml bed volume) of Sephadex A-25 equilibrated with 20 mM TEAB. The column was washed with the same buffer and then developed with a gradient of 0.15–0.8 M TEAB. 5-Thiol UTP was eluted at 0.46–0.52 M salt. The peak fractions were combined and lyophilized, and the resulting powder was resuspended in water and re-lyophilized. This procedure was repeated 4–5 times until most of the salt evaporated. The structure of the product was confirmed by 2D PMR spectroscopy.

Example 2

Synthesis of thiolated ATP (Scheme 4)

2a. Synthesis of $N^6$-(carboxymethyl)ATP

The synthesis was adopted from Gebeyehu et al. (Gebeyehu et al., 1987). A mixture of ATP (98.1 mg) and sodium iodoacetate (333 mg) in 3.37 ml $H_2O$ at pH 6.5 was stirred at for 4 days at 30° C. The reaction mixture was cooled and poured onto 100 ml of chilled ethanol. The precipitate was collected and dissolved in 12 ml of $H_2O$. The pH was adjusted to 8.5 with 0.1 M NaOH, the solution was heated to 90° C. for 1 h, cooled to room temperature and loaded on a column of Sephadex A-25 (20 ml bed volume) which had been equilibrated with 0.1 M TEAB. After washing with 0.1 M TEAB, a step gradient from 0.1 to 0.5 M TEAB in 100 ml increments was applied. The starting material eluted at 0.4–0.5 M salt. $N^6$-(carboxymethyl)ATP was then eluted with 1 M TEAB. The material was lyophilized and analyzed by NMR and TLC.

2b. Synthesis of $N^6$-[(6-aminohexyl)carbamoylmethyl]-ATP $N^6$-(carboxymethyl)ATP (15 mg) was dissolved in 0.48 ml of a 1 M aqueous solution of 1,6 diaminohexane adjusted to pH 4.7 with 5 M HCl. Ethyldimethylaminopropyl carbodiimide (EDC) (5 mg) was added and the mixture was stirred for 2 h. Two additional portions of EDC (5 mg each) were added at 30 min intervals. The reaction mixture was cooled on ice and added to 20 ml of a chilled 1:1 mixture of acetone and ethanol. The precipitate was collected, dissolved in water and loaded on a column of Sephadex A-25 (20 ml bed volume) which had been equilibrated with 20 mM TEAB. After washing with 20 mM TEAB, a step gradient from 0.1 to 0.5 M TEAB in 100 ml increments was applied. The $N^6$-[(6-aminohexyl)carbamoylmethyl]-ATP was eluted at 0.5 M salt. The product was analyzed by TLC and NMR.

2c. Synthesis of Thiol-ATP

Thiolation of $N^6$-[(6-aminohexyl)carbamoylmethyl]-ATP with 2-iminothiolane was carried out as described above for 5-thiol-UTP. Thiol-ATP was purified by anion exchange chromatography on Sephadex A-25 using a linear gradient of 0.15–0.7 M TEAB. Thio-ATP eluted at 0.5–0.55 M salt and recovered by lyophilization.

Example 3

Synthesis of thiol-AMP-PCP

The synthesis of thiol-AMP-PCP (the unhydrolyzable analog of thiol-ATP) was carried out as described above for thiol-ATP starting from AMP-PCP.

Example 4

Synthesis of thiolated 2'(3'),5'-biphosphocytidine (thiol-pCp) (Scheme 5)

4a. Synthesis of pCp

The synthesis of pCp was as described by Hall and Khorana 1955. In brief, cytidine (1 gr) was mixed with 5 ml of phosphorylation reagent and incubated at 60° C. in a sealed glass tube for 20 h. Phosphorylation reagent was prepared by dissolving 5 gr of $P_2O_5$ in 3.75 ml of 85% $H_3PO_4$. The reaction mixture was diluted with 60 ml of water, the pH was adjusted to 2.1 with 5 M HCl, and boiled for 15 min. The chilled solution was neutralized (pH 9) with 4.5 M LiOH and loaded onto a column of Dowex 2×8 (50 ml bed volume) that had been equilibrated with 20 mM ammonium bicarbonate (AMBIC). The column was washed with 20 mM AMBIC until all remaining starting material was eluted, and then developed with a linear gradient of 0.1–0.8 M AMBIC. The product pCp eluted at 0.6 . 0.7 M AMBIC and was recovered by lyophilization.

4b. Synthesis of $N^4$-(6-aminohexyl)-pCp pCp (0.4 gr) was dissolved in 2 ml of $H_2O$ and mixed with 8 ml of a 3.7 M solution of 1,6 bisaminohexane (pH 7.2). An aqueous solution of $Na_2S_2O_5$ (2.3 gr in 3 ml $H_2O$) was added to the reaction mixture simultaneously with 14 mg of hydroquinone dissolved in a minimum volume of ethanol. The reaction mixture was stirred at 42° C. for 15 h, cooled on ice, and mixed with 40 ml of ice cold ethanol. The precipitate was collected, dissolved in $H_2O$ and loaded onto a column of Sephadex A-25 (50 ml bed volume) that had been equilibrated with 20 mM TEAB. The column was washed with 20 mM TEAB and then developed with a linear gradient of 0. 15–0.6 M TEAB. $N^4$-(6-aminohexyl)pCp eluted at 0.3–0.35 M salt. After lyophilization the product was characterized by PMR and $^{31}$P-NMR. The example given is with 1,6diaminohexane (n=6) but transamination can be done with any diamine $H_2N-(CH2)_n-NH_2$.

4c. Synthesis of Thiolated pCp

Thiolation of $N^4$-(6aminohexyl)-pCp with 2-iminothiolane was carried out as described above for 5-thiol-UTP. The product was purified by anion exchange chromatography on Sephadex A-25 as described above for $N^4$-(6-aminohexyl)-pCp. Thiolated pCp eluted at 0.36–0.45 M salt, recovered by lyophilization, and characterized by 2D NMR.

Example 5

Randomly Thiolated RNA

RNA is normally prepared in vitro by transcribing a plasmid containing the DNA encoding for the desired RNA in the presence of the four rNTPs. Modified RNAs can be prepared by substituting a modified rNTP for all. or for part, of the particular one from which it was derived. The density of modification can be determined by controlling the ratio of modified to normal rNTP in the transcription reaction. As a prototype example of this strategy we describe below the preparation of gold-containing β-globin RNA with thiol-UTP as the modified NTP. Analogous procedures will be used to prepare RNA in which gold clusters are attached to adenine or cytidine residues starting from thiol-ATP and thiol-CTP, respectively.

A standard transcription in vitro reaction catalyzed by SP6 RNA polymerase was carried out using the template plasmid pSP64HbΔ6 cut with BamHI, which yields a 497-nt long RNA containing the first two exons and the intervening intron of the β-globin gene. In addition to ATP, GTP, CTP, and UTP, the reaction mixture contained 10% thiol-UTP (UTP:thiol-UTP =9:1) and $^{32}$P-labeled ATP as a radioactive tracer. The RNA was recovered by phenol extraction and ethanol precipitation.

Coupling of thiolated RNA to monomaleimido NANOGOLD (Nanoprobe, Stony Brook N.Y.) was carried out according to the manufacturer instructions. Precipitation with ethanol gave an RNA preparation free of the reagent. The RNA was subjected to electrophoresis on an agarose gel and transferred to a nitrocellulose membrane. The gold-containing RNA was revealed by silver enhancement (FIG. 1, lanes 1–3) whereas unmodified RNA which had been treated with monomaleimido NANOGOLD did not stain at all (FIG. 1, lane 4). The electrophoretic mobility of the modified RNA corresponds to an RNA of about 700 nt. It can thus be estimated that the mass of the 497-nt β-globin RNA (~150 kDa) increased by ~60 kDa. Since the molecular mass of NANOGOLD is not known it is not possible to estimate the number of gold clusters per RNA molecule. However, if we assume that NANOGOLD has twice the mass of undecagold (6,000 Da), an estimate of ~5 clusters per RNA can be made. This is a reasonable estimate, given that the maximum number of thiolated uridines in the RNA is 12 (10% of ~125) and that the efficiency of incorporation of thiol-UTP into the RNA is expected to be substantially smaller than that of UTP.

Preliminary visualization of gold-RNA by bright field transmission electron microscopy (TEM) (FIG. 2) showed gold particles arranged at regular distances on a (imaginary) curve, while a control of unmodified RNA which had been treated with monomaleimido NANOGOLD gave no signal at all. FIG. 3 is an AFM image showing unmodified RNA (a); gold labeled single stranded RNA (b); and gold labeled double stranded RNA (c).

Example 6

Gold-tagged β-globin RNA

The plasmid pSP64HβΔ6, which contains the human β-globin gene (Krainer et al., 1984), was linearized with BamHI and transcribed in vitro to yield a 497-nt transcript comprising the first two exons and the first intron of β-globin. A standard transcription reaction mixture (in a total volume of 20 μl) contained 40 mM Tris-HCl, pH 7.9, 10. mM NaCl, 6 mM $MgCl_2$, 20 mM DTT, 2 mM spermidine, 20 units ribonuclease inhibitor (MBI Fermentas), 1 μg linearized DNA, 0.5 mM each of ATP, GTP, UTP, and CTP, and 40 units of SP6 RNA polymerase (MBI Fermentas). For the preparation of thiolated RNA, UTP-SH or ATP-SH was added to the transcription reaction mixture (the syntheses of the thiolated nucleoside triphosphates, UTP-SH and ATP-SH, will be published elsewhere). Transcription was carried out for 1 h at 37° C., and the resulting 497-nt RNA was recovered by phenol extraction and ethanol precipitation.

The thiolated RNA was resuspended in 50 μl of 0.1 M sodium phosphate, pH 6.4, containing 1 mM EDTA and 2 mM vanadyl ribonucleoside complex (Chirgwin et al., 1979) as an RNase inhibitor. One nanomole monomaleimido NANOGOLD (Nanoprobes, estimated 10-fold excess) was added and the reaction mixture was incubated for 6 h at 4° C. The gold-tagged RNA was recovered by two ethanol precipitations.

6a. Transmission Electron Microscopy

RNA was dissolved in water and deposited on ultrathin carbon films that spanned holey carbon-coated copper grids. Excess solution was blotted with a wet filter paper and the grids were imaged in a Philips CM-12 TEM operating at 100 kV.

6b. Atomic Force Microscopy

RNA samples were pipetted onto a chip of freshly cleaved mica and covered with a second chip that had been washed with pure water (Milli-Q Plus system). The RNA suspension was incubated for 5–10 min and then the mica sheets were separated and one of them was brought into contact with pure water. Finally, the bulk fluid on the sample was removed quickly with a stream of wet nitrogen. The samples were probed in air with a Nanoscope III AFM instrument (Digital Instruments, Santa Barbara, Calif.) operating in the tapping mode.

Example 7

Concluding Remarks and Discussion

Thus, to verify the feasibility of the approach to covalently tag nucleic acids, RNA in the above Examples, with, for example, gold clusters, whether NANOGOLD can be covalently incorporated into a pre-mRNA molecule and then visualized by TEM was put to test. RNA is normally prepared in vitro by transcribing a plasmid containing the DNA encoding the desired RNA in the presence of RNA polymerase and all four ribonucleoside triphosphates (rNTPs). Modified RNAs can be prepared by substituting a modified rNTP for all, or for part, of the particular rNTP from which it was derived. The density of modification can thus be determined by choosing the ratio of modified to normal rNTP in the transcription reaction. Although most commercial RNA polymerases recognize modified rNTPs, even with bulky substituents such as biotin (e.g., Langer et al. 1981), without being limited by any theory, it is conceivable that a rNTP attached to a gold cluster with a diameter of 1.4 nm would not be as efficiently recognized by the enzyme. Therefore, first, modified rNTP containing free thiol groups were incorporated into the RNA and then it was coupled to a maleimido-gold cluster (monomaleimido NANOGOLD). This general strategy is schematically depicted in FIG. 1, and as a prototype example we describe below the preparation and visualization by TEM and Aof gold-tagged β-globin RNA.

Thiolated β-Globin RNA

The plasmid pSP64HβΔ6, which contains the human β-globin gene (Krainer et al, 1984), was linearized with BamHI and transcribed in vitro with SP6 RNA polymerase to yield a β-globin pre-mRNA like molecule harboring the β-globin first two exons and the intervening intron. To prepare thiolated β-globin RNA, the linearized β-globin plasmid was transcribed in vitro with SP6 RNA polymerase in the presence of all four rNTPs and a UTP analog containing a substituent with a terminal thiol group on its heterocyclic ring (UTP-SH; 5, 10, or 50% of total input UTP). To verify that UTP-SH was indeed incorporated into the RNA, we performed in parallel a second identical transcription reaction except that [α-$^{32}$P]ATP was added as a radioactive tracer. The labeled RNA was recovered by phenol extraction and ethanol precipitation and coupled to biotin using 1-biotin-4- [4'-maleimidomethyl) cyclohexanecarboxyamido]butane (Biotin-BMCC, Pierce), and the resulting RNA was bound to immobilized monomeric avidin (Pierce). Elution of the bound material with D-biotin showed that 85% of the input $^{32}$P-labeled RNA was specifically and reversibly retained on the solid matrix, indicating that the transcribed RNA contained thiolated nucleotides.

A similar protocol was used to prepare β-globin RNA with thiolated adenosine residues. In that case, the transcription reaction was carried out in the presence of all four rNTPs and an ATP analog containing a substituent with a terminal thiol group on its heterocyclic ring (ATP-SH; 10 or 50% of total input ATP).

Gold-Tagged β-Globin RNA

Figure 2:
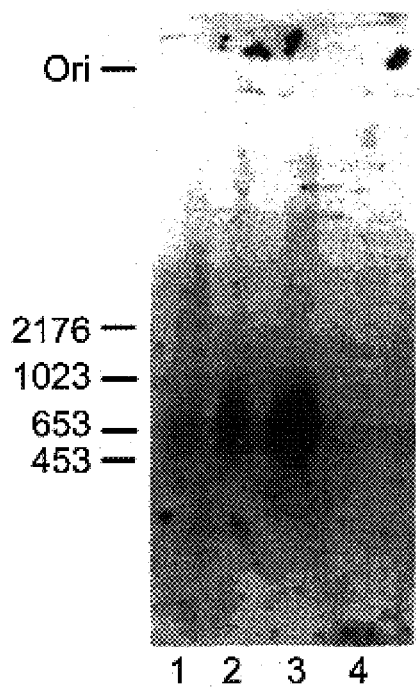
FIG. 2 Gel electrophoresis of gold-tagged RNA. β-globin pre-mRNA was transcribed in the presence of UTP-SH (10% of total input UTP). Increasing amounts (5–15 ng) of the gold-tagged β-globin pre-mRNA (lanes 1–3) along with unmodified β-globin pre-mRNA (lane 4) were subjected to electrophoresis on a 2%-agarose gel and transferred to a nitrocellulose membrane, and gold-containing bands were revealed by silver enhancement. Response to this treatment, in a quantity dependent manner, is seen only in lanes where gold-RNA is present. The unmodified β-globin pre-mRNA of 497 bases (lane 4) is not seen. The origin and the migration of size markers (in number of bases) are indicated on the left.

Coupling of thiolated (UTP-SH) β-globin RNA to monomaleimido NANOGOLD was carried out according to the manufacturer's instructions. Precipitation with ethanol gave an RNA preparation free of the reagent. To demonstrate that NANOGOLD was covalently bound to the RNA, the RNA was subjected to electrophoresis on an agarose gel and transferred to a nitrocellulose membrane. The gold-containing RNA was revealed by silver enhancement (Burry et al., 1992) (FIG. 2, lanes 1–3), whereas unmodified RNA that had been treated with monomaleimido NANOGOLD did not stain at all (FIG. 2. lane 4). The apparent electrophoretic mobility of the modified RNA corresponds to RNA of about 700 nucleotides (nt). It can thus be estimated that the mass of the 497-nt β-globin RNA (~150 kDa) increased by ~60 kDa. Since the molecular mass of NANOGOLD is not known, it is not possible to estimate the number of gold clusters per RNA molecule. However, if we assume that NANOGOLD has twice the mass of undecagold (6000 Da), an estimate of ~5 clusters per RNA can be made. This is a reasonable estimate, given that the maximum number of thiolated uridines in the RNA is 12 (10% of ~125) and that the efficiency of incorporation of thiol-UTP into the RNA is expected to be substantially smaller than that of UTP.

Visualization of Gold-Tagged β-Globin RNA by TEM

Visualization of unstained gold-tagged β-globin RNA by bright field TEM showed spots of gold clusters. with a diameter of 1–2 nm, arranged at nearly regular distances on an imaginary curve (FIGS. 3b and 3c). The apparent variability in the size of these spots is similar to that observed in TEM images of NANOGOLD and may thus reflect size variations in a particular batch of the reagent. Though the organic shell of NANOGOLD is expected to completely eliminate aggregation of these clusters (Hainfeld and Furuya, 1992), the extremely large spot in FIG. 3b may be attributed to an aggregate that could have been formed during sample manipulations. Notably, the density of gold clusters along these curves corresponds to the proportion of NTP-SH that was present in the transcription reaction. Thus, gold clusters in β-globin RNA that was transcribed in the presence of 10% ATP-SH (10% of total input ATP; FIG. 3b) are more spread than those in β-globin RNA that was transcribed in the presence of 50% UTP-SH (50% of total input UTP; FIG. 3c). In a control experiment, where unmodified RNA had been treated with monomaleimido NANOGOLD and then manipulated in exactly the same manner as in experiments with thiolated RNA, a signal of scattered gold clusters could only rarely be observed by bright-field TEM (FIG. 3a).

Visualization of Gold-Tagged β-Globin RNA by AFM

Direct evidence for the attachment of gold clusters at random locations on the RNA was achieved by the simultaneous visualization of RNA and gold clusters by AFM imaging. Diluted RNA samples were deposited on freshly cleaved mica chips, dried in air, and imaged in air (FIG. 4). The AFM images of single-stranded β-globin RNA (FIG. 4) correspond to an apparent height of about 0.7 run. This value is significantly smaller than 1.6 nm which is the expected diameter based on X-ray crystal structure data for the single-stranded helical form of poly(A) (Saenger, 1984a,b). On the other hand, it is similar to the height of 0.7±0.1 nm that was observed by AFM for poly(A) RNA (Smith et al., 1997), indicating that compression of the RNA occurred upon depositing and drying on the mica. The end to end length in each of the RNA images was estimated from measurements of their contour length using the NIH Image package and was found to range between 350 and 400 nm. For a 497-nt long RNA, this value corresponds to a nucleotide to nucleotide distance of 0.7–0.8 nm, more than two times larger than the 0.282 nm axial rise per nucleotide in single-stranded helical poly(A) RNA (Saenger, 1984b). This observation indicates that stretching of the helical RNA molecules occurred during the sample preparation for the AFM and is consistent with the observed reduction in their diameter.

Figure 5:
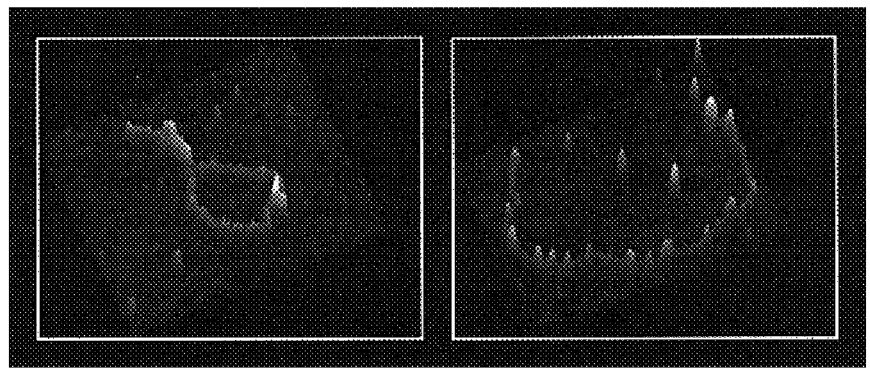
FIG. 5 Surface plot of AFM images. The surface plots were drawn from the respective AFM images shown in FIG. 4 using the "surface plot" function of the NIH Image package. (Left) Unmodified single-stranded RNA (corresponding to FIG. 4a, left). (Right) Gold-labeled single-stranded RNA (corresponding to FIG. 4b, right).

Notwithstanding, single-stranded gold-tagged β-globin RNA molecules exhibit images in which knob-like structures are clearly seen along the RNA chai (FIG. 4b). The height of the brightest knobs (typical knobs are indicated by arrows in FIG. 4b) range between 1.7 and 2.5 nm. This value is in agreement with the height observed for free NANOGOLD (2.0–2.6 nm). The distinction between the apparent uniform height of unmodified RNA and the spiky appearance of the gold-labeled RNA can clearly be seen in the surface plot of the respective RNAs (FIG. 5). These knobs are thus attributed to gold clusters attached to the RNA chain.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.
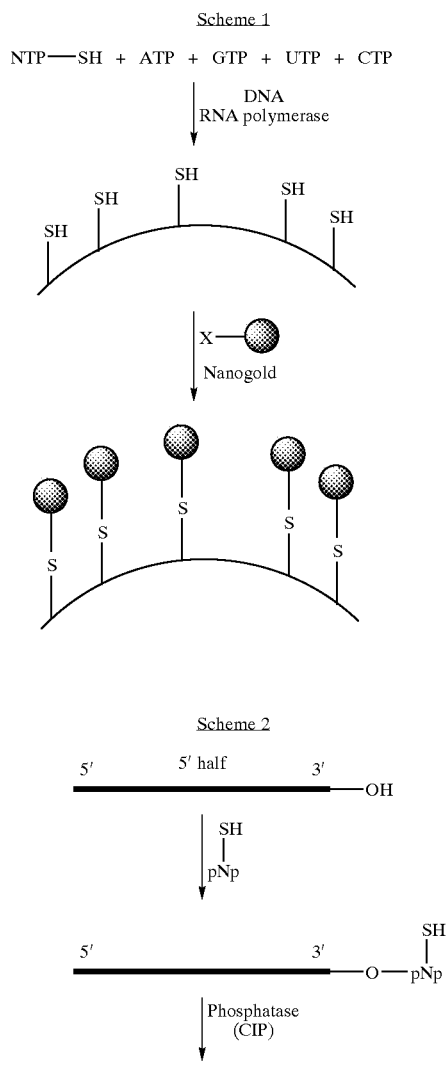
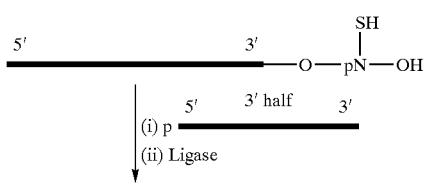
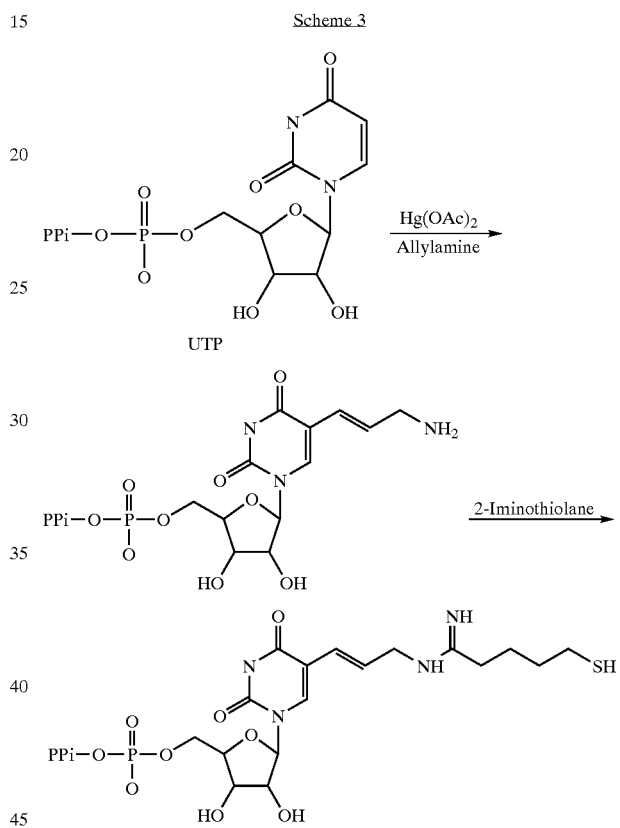
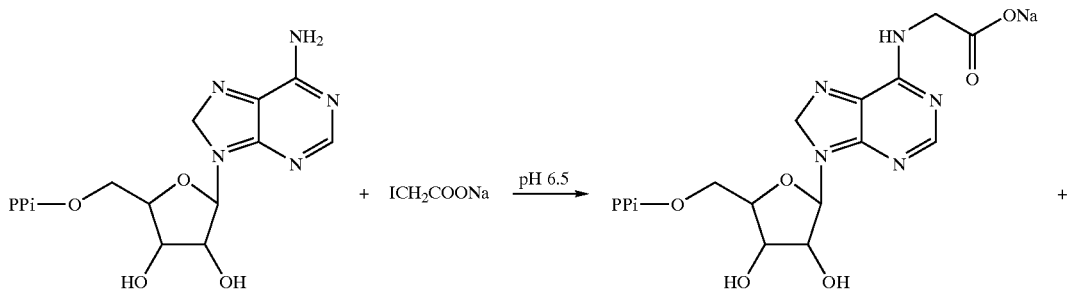

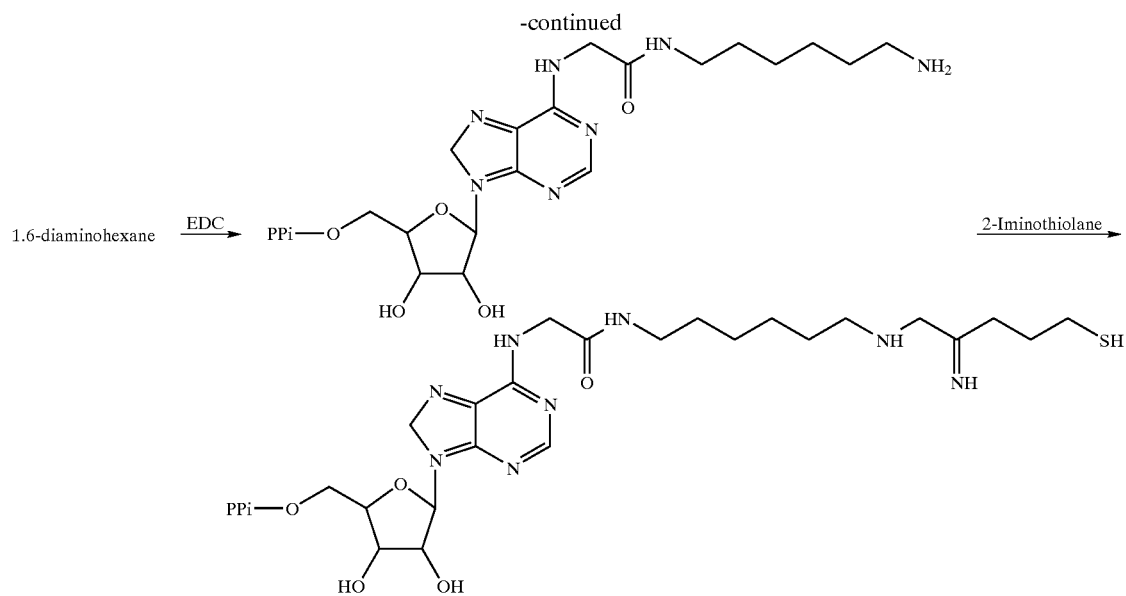
Scheme 5
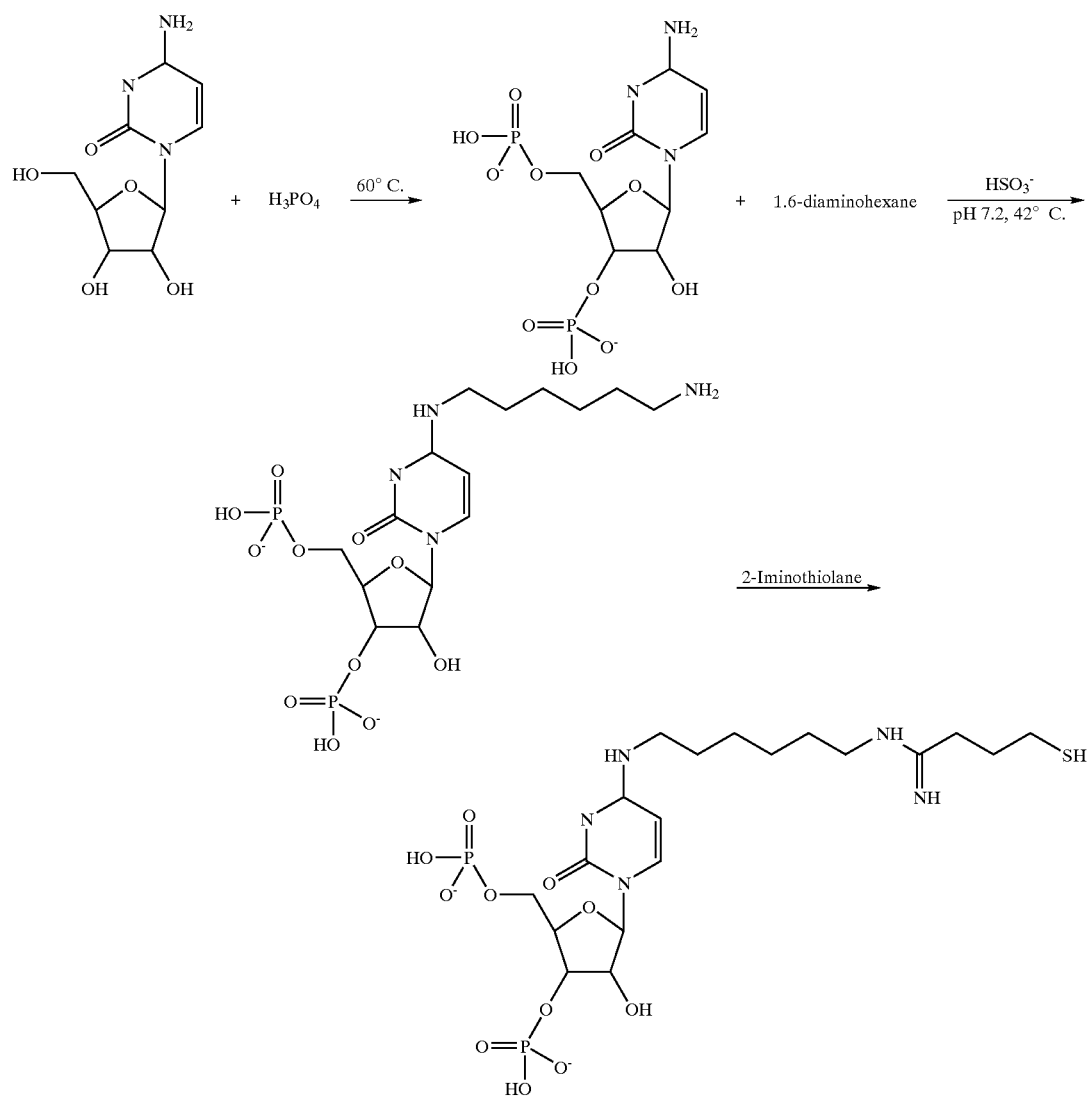

References

Alivisatos, A. P, Johnsson, K. P., Peng, X., Wilson, T. E., Loweth, C. J., Bruchez, M. J., and Schultz, P. G. (1996) Organization of 'nanocrystal molecules' using DNA. Nature 382, 609–611.

Bazett-Jones, D. (1992) Electron spectroscopic imaging of chromatin and other nucleoprotein complexes. Electron Microsc Rev 5, 37–58.

Benner, S. A. (1995). Method for incorporation into a DNA or RNA oligonucleolide using nucleotide bearing heterocyclic bases. U.S. Pat. No. 5,432,272.

Boisset, N., Grassucci, R., Penczek, P., Delain, E., Pochon, F., Frank, J., and Lamy, J. N. (1992) Three-dimensional reconstruction of a complex of human alpha 2-macroglobulin with monomaleimido NANOGOLD (Aul .4nm) embedded in ice. J. Struct. Biol. 109, 3945.

Burry, R. W., Vandre, D. D., and Hayes, D. M. (1992) Silver enhancement of gold antibody probes in pre-embedding electron microscopic immunocytochemistry. J His-tochem. 40, 1849–1856.

Chirgwin, J. M, Przbyla, A. E., MacDonald, R. J., and Rutter, W. J. (1979) Isolation of biologically active ribonucleic acid from sources enriched in ribonuclease. Biochemistry 18, 5294–5299.

Chiu, W., and Schmid, M. F. (1997) Pushing back the limits of electron cryomicroscopy, Nat. Struct. Biol. 4, 331–333. [news]

Dubochet, J., Ducommun, M., Zollinger, M., and Kellenberger, E. (1971) A new preparation method for dark-field electron microscopy of biomacromolecules. J Ultrastruct. Res. 35, 147–167.

Earnshaw, D. J., and Gait, M. J. (1998). Modified oligoribonucleotides as site-specific probes of RNA structure and function. Biopolymers 48,39–55.

Eaton, B. E. (1997). The joys of in vitro selection: chemically dressing oligonucleotides to satiate protein targets. Curr Opin Chem Biol 1, 10–16.

Gebeyehu, G., Rao, P. Y., SooChan, P., Simms, D. A., and Klevan, L. (1987). Novel biotinylated nucleotide-- analogs for labeling and colorimetric detection of DNA. Nucleic Acids Res. 15, 4513–4534.

Griffith, J. D., Lee, S. and Wang, Y. H. (1997) Visualizing nucleic acids and their complexes using electron microscopy. Curr. Opin. Struct. Biol. 7, 362–366.

Guckenberger, R., Heim. M., Cevc, G., Knapp, H. F., Wiegrabe, W., and Hillebrand, A. (1994) Scanning tunneling microscopy of insulators and biological specimens based on lateral conductivity of ultrathin water films. Science 266, 1538–1540.

Hainfeld, J. F., and Furuya, F. R. (1992) A 1.4-nm gold cluster covalently attached to antibodies improves immunolabeling. J. Hislochem. Cylochem. 40, 177–184.

Hansma, H. G., Revenko., I., Kim, K., and Laney, D. E. (1996) Atomic force microscopy of long and short double-stranded. single-stranded and triple-stranded nucleic acids. Nucleic Acids Res. 24, 713–720.

Krainer, A. R., Maniatis, T., Ruskin, B., and Green, M. R. (1984) Normal and mutant human β-globin pre-mRNAs are faithfully and efficiently spliced in vitro. Cell 36, 993–1005.

Langer, P. R., Waldrop, A. A., and Ward, D. C. (1981) Enzymatic synthesis of biotin-labeled polynucleotides: Novel nucleic acid affinity probes. Proc. Natl. Acad. Sci. USA 78,6633–6637.

Muller, S., Wolpensinger. B., Angenitzki, M., Engel, A., Sperling, J., and Sperling, R. (1998) A supraspliceosome model for large nuclear ribonucleoprotein particles based on mass determinations by scanning transmission emicroscopy. J. Mol Biol. 283, 383–394.

Saenger, W. (1984a) RNA Structure, in Principles of Nucleic Acid Structure, pp. 242–252, Springer-Verlag, New York.

Saenger, W. (1984b) Synthetic, homopolymer nucleic acids structures, in Principles of Nucleic Acid Structure, pp. 298–320, Springer-Verlag, New York.

Safer, D., Bolinger, L., and Leigh, J. S. J. (1986) Undecagold clusters for site-specific labeling of biological macromolecules: Simplified preparation and model applications. J. Inorg. Biochem. 26, 77–91.

Sakthivel, K., and Barbas, C. F. (1 998). Expanding the potential of DNA for binding and catalysis: Highly functionalized dUTP derivatives that are substrates for thermostable DNA polymerases. Angew Chem Int Ed Engl 37, 2872–2875.

Sibbald, M. J., Carlemalm, E. C., Beer, M., and Sproat, B. S. (1993) Imaging of RNA-protein interactions in splicing complexes with dark-field STEM. J. Struct. Biol. 110, 111–121.

Smith, B. L., Gallie, D. R. Le, H., and Hansma, P. K. (1997) Visualization of poly(A)-binding protein complex formation with poly(A) RNA using atomic force microscopy. J. Struct. Biol 119, 109–117.

Wang, Y.-H., Murphy, F. L., Cech, T. R., and Griffith, J. D. (1994) Visualization of a tertiary structural domain of the Tetrahymena group I intron by electron microscopy. J. Mol. Biol. 236, 64–71.

Weinstein, S., Jahn, W., Hansen, H. A. S., Wittmann, H. G., and Yonath, A. (1989) Novel procedures of derivatization of ribosomes for crystallographic studies. J. Biol. Chem. 264, 19138–19142.

Weinstein, S., Jahn, W., Laschever, M., Arad, T., Tichelaar, W., Haider, M., Glotz, C., Boeckh, T., Berkovitch-Yellin, Z., Franceschi, F., and Yonath, A. (1992) Derivatization of ribosomes and of tRNA with an undecagold cluster: Crystallographic and functional studies. J. Crystal Growth 122, 286–292.

Wenzel, T., and Baumeister, W. (1995) Conformational constraints in protein degradation by the 20S proteasome. Nat. Struct. Biol. 2, 199–204.

What is claimed is:

1. A nucleotide comprising a sugar moiety selected from a natural sugar moiety and a sugar analog thereof, a natural phosphodiester or any other internucleosidyl linkage, and a natural pyrimidine or purine base or a base analog thereof, and a terminal thiol group at a side chain being covalently linked to the pyrimidine or purine base or base analog of the nucleotide, said side chain having at least 7 carbon atoms, is interrupted by at least one heteroatom selected from the group consisting of O, S and N and is substituted by at least one =NH group.

2. The nucleotide of claim 1, comprising a natural sugar moiety, a natural phosphodiester linkage, and a natural pyrimidine or purine base, and a terminal thiol group at a side chain being covalently linked to the pyrimidine or purine base of the nucleotide.

3. The nucleotide of claim 1, wherein the sugar moiety is ribose.

4. The nucleotide of claim 1, wherein the sugar moiety is deoxyribose.

5. The nucleotide of claim 1, wherein the sugar moiety is dideoxyribose.

6. The nucleotide of claim 1, which is a monophosphate, diphosphate, 3',5'-bisphosphate or 5'-triphosphate.

7. The nucleotide of claim 1, wherein said side chain is saturated or unsaturated and has 7–20 carbon atoms.

8. the nucleotide of claim 7, wherein said saturated or unsaturated side chain has 7–15 carbon atoms.

9. The nucleotide of claim 1, further comprising a metal cluster being covalently linked through said terminal thiol group at said side chain to the pyrimidine or purine base of the nucleotide.

10. The nucleotide of claim 9, wherein said metal is Ag, Au, Hg, Pt, Mo or W.

11. The nucleotide of claim 10, wherein said metal is Au.

12. The nucleotide of claim 11, wherein said metal cluster is colloidal gold.

13. A nucleic acid comprising at least one nucleotide of claim 1.

14. The nucleic acid of claim 13, comprising ribonucleotides.

15. The nucleic acid of claim 13, comprising deoxyribonucleotides.

16. The nucleic acid of claim 13, wherein said at least one nucleotide further includes a metal cluster covalently linked through said terminal thiol group at said side chain to the pyrimidine or purine base or base analog of the nucleotide.

17. The nucleic acid of claim 16, wherein said metal is Ag, Au, Hg, Pt, Mo or W.

18. The nucleic acid of claim 17, wherein said metal is Au.

19. The nucleic acid of claim 18, wherein said metal cluster is colloidal gold.

20. A method for labeling a nucleic acid molecule at random locations with a metal, the method comprising incorporating a thiolated nucleotide according to claim 1 into said nucleic acid molecule, and attaching the metal atoms to the free thiol groups of the thiolated nucleic acid.

21. The method of claim 20 for the attachment of gold-clusters at random locations in a nucleic acid molecule, comprising:

(i) preparation of precursor deoxyribonucleoside triphosphates (NTPs) and ribonucleoside triphosphates (rNTPs) whose heterocyclic ring contains substituents with a terminal thiol group (NTP-SH and rNTP-SH, respectively);

(ii) incorporation of these precursor molecules into DNA or RNA in reactions catalyzed by DNA polymerase or RNA polymerase, respectively; and (iii) attachment of gold-clusters to the free thiol groups, either by reacting with a commercially available maleimido derivative of the cluster, or by reacting with colloidal gold of pre-determined size.

* * * * *